(12) United States Patent
Park et al.

(10) Patent No.: US 10,913,702 B2
(45) Date of Patent: Feb. 9, 2021

(54) METHOD FOR CYCLOADDITION OF DIMETHYL MUCONATE

(71) Applicant: SK CHEMICALS CO., LTD., Seongnam-si (KR)

(72) Inventors: Jae Kyun Park, Seoul (KR); Jeong Ho Park, Seongnam-si (KR); Hee-il Chae, Seongnam-si (KR)

(73) Assignee: SK CHEMICALS CO.. LTD., Seongnam-si (KR)

( * ) Notice: Subject to any disclaimer, the term of this patent is extended or adjusted under 35 U.S.C. 154(b) by 0 days.

(21) Appl. No.: 16/771,999

(22) PCT Filed: Dec. 14, 2018

(86) PCT No.: PCT/KR2018/015885
§ 371 (c)(1),
(2) Date: Jun. 11, 2020

(87) PCT Pub. No.: WO2019/139264
PCT Pub. Date: Jul. 18, 2019

(65) Prior Publication Data
US 2020/0399201 A1    Dec. 24, 2020

(30) Foreign Application Priority Data

Jan. 15, 2018 (KR) .......... 10-2018-0004978

(51) Int. Cl.
C07C 67/347 (2006.01)
C07C 67/475 (2006.01)
C07C 69/017 (2006.01)
C07C 69/82 (2006.01)

(52) U.S. Cl.
CPC .......... C07C 67/347 (2013.01); C07C 67/475 (2013.01); C07C 69/017 (2013.01); C07C 69/82 (2013.01)

(58) Field of Classification Search
CPC ... C07C 67/347; C07C 67/475; C07C 69/016; C07C 69/82
See application file for complete search history.

(56) References Cited

U.S. PATENT DOCUMENTS 8,426,639 B2 * 4/2013 Frost .................. C07C 67/317
562/591
2011/0288311 A1  11/2011 Frost et al.

FOREIGN PATENT DOCUMENTS

| CN | 106467466 A | 3/2017 |
| KR | 10-2012-0027531 A | 3/2012 |
| KR | 10-2017-0047802 A | 5/2017 |
| WO | 2012/082725 A1 | 6/2012 |

OTHER PUBLICATIONS

Dr. Erisa Saraci et al., "Bioderived Muconates by Cross-Metathesis and Their Conversion into Terephthalates", ChemSusChem., 2018, pp. 773-780, vol. 11, No. 4.
International Search Report for PCT/KR2018/015885 dated Mar. 21, 2019 (PCT/ISA/210).

* cited by examiner

*Primary Examiner* — Yate' K Cutliff
(74) *Attorney, Agent, or Firm* — Sughrue Mion, PLLC

(57) ABSTRACT

A method for cycloaddition of dimethyl muconate is disclosed. According to the method, a direct transferring of a solid phase trans,trans-dimehtyl muconate into a reactor pre-filled with ethylene gas increases the efficiency of the reaction and suppress side reactions resulting an improvements in yield and purity. Furthermore, the method is capable of obtaining a high yield of dimethylcyclohex-2-en-1,4-dicarboxylate at a lower cost, and therefore is also useful for the mass synthesis of dimethyl terephthalate.

12 Claims, No Drawings

METHOD FOR CYCLOADDITION OF DIMETHYL MUCONATE

CROSS REFERENCE TO RELATED APPLICATIONS

This application is a National Stage of International Application No. PCT/KR2018/015885 filed Dec. 14, 2018, claiming priority based on Korean Patent Application No. 10-2018-0004978, filed Jan. 15, 2018.

TECHNICAL FIELD

The present invention relates to a process for cycloaddition of dimethyl muconate. More specifically, the present invention relates to a process for effective cycloaddition of trans,trans-dimethyl muconate to obtain dimethylcyclohex-2-ene-1,4-dicarboxylate in a high yield.

BACKGROUND ART

In recent years, technologies to replace petroleum-derived substances with bio-derived substances have been studied. For example, the oil extracted from plants such as rapeseed oil, soybean oil, and palm oil is converted into biodiesel or the like to be used in diesel engines through an esterification reaction. In addition, bio-derived substances are being studied not only for the above materials for energy, but also as raw materials for the traditional polymer industry. Representatively, polylactic acid (PLA), a biodegradable polymer using lactic acid as a raw material, is currently commercialized.

In addition, polytrimethylene terephthalate (PTT) obtained by polymerizing a bio-derived 1,3-propanediol with an acid compound is a typical example of polyesters that have reached the commercialization stage. Meanwhile, dimethyl terephthalate (DMT, chemical formula of $C_{10}H_{10}O_4$, molecular weight of 194) is mainly used as an acid compound in the production of such polyesters. In addition, DMT is used in various fields such as the production of plastics, coatings, adhesives, and paints that use polyesters, or the synthesis of various types of dialcohols through reduction.

Such DMT may be obtained through the synthesis of dimethylcyclohexene-1,4-dicarboxylate through a cycloaddition reaction of dimethyl muconate, followed by an aromatization reaction thereof. According to International Patent Publication No. WO 2012/082725, trans,trans-dimethyl muconate is dissolved in a solvent and introduced to a reactor, followed by injection of ethylene gas to carry out a cycloaddition reaction to synthesize dimethylcyclohex-2-ene-1,4-dicarboxylate used in the production of DMT.

However, this conventional process of cycloaddition has a disadvantage that it cannot proceed with the reaction at a high concentration. If the concentration of the reactants is increased to solve this problem, too many side reactants take place. If the reaction temperature is lowered to reduce the side reactions, the cycloaddition reaction is not carried out well. In addition, according to the conventional process, a long reaction time is required even at a low concentration, so that the efficiency is reduced. As a result, it is not desirable from the economical point of view that the operability in the production of commercial products is lowered.

DISCLOSURE OF INVENTION

Technical Problem

While the present inventors have been studying to solve the above-mentioned problems, it has been discovered that when trans,trans-dimethyl muconate in a solid phase is directly introduced to a reactor filled with ethylene gas in advance, an efficient cycloaddition reaction may take place even under high-concentration conditions.

Thus, an object of the present invention is to provide an efficient process for cycloaddition of dimethyl muconate in a high yield even under high-concentration conditions.

Solution to Problem

According to the above object, the present invention provides a process for cycloaddition of dimethyl muconate, which comprises (1) preparing a reactor filled with ethylene gas; and (2) introducing a compound of the following Formula 1 in a solid phase to the reactor and carrying out a cycloaddition reaction to obtain a compound of the following Formula 2.

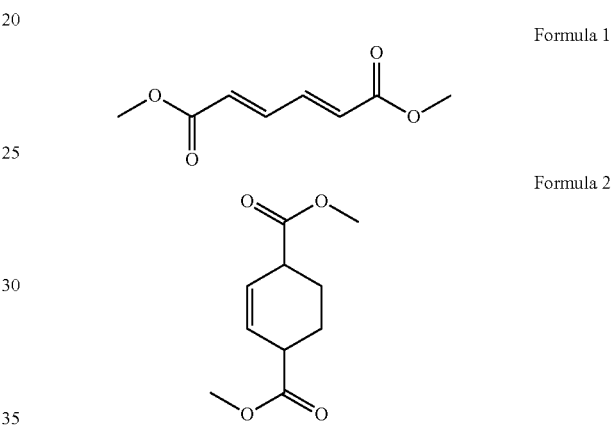

In addition, the present invention provides a process for preparing dimethyl terephthalate, which comprises (1) preparing a reactor filled with ethylene gas; (2) introducing a compound of the above Formula 1 in a solid phase to the reactor and carrying out a cycloaddition reaction to obtain a compound of the above Formula 2; and (3) obtaining dimethyl terephthalate from the compound of Formula 2 through an aromatization reaction.

Advantageous Effects of Invention

According to the process of the present invention, it is possible to efficiently carry out the cycloaddition reaction of dimethyl muconate as compared with the prior art. As a result, it is possible to attain a high yield and purity even under high-concentration reaction conditions.

In particular, in the conventional process in which ethylene gas is injected after a high concentration of dimethyl muconate is dissolved in a solvent, the yield is low due to many side reactions. According to the present invention, however, since dimethyl muconate in a solid phase is introduced to a reactor filled with ethylene gas in advance, an efficient cycloaddition reaction may take place even under high-concentration conditions without side reactions. Thus, it is possible to obtain the desired target compound in a high yield.

In addition, according to the present process, it is advantageous from the economic point of view that it can achieve the same level of reaction efficiency as in the prior art even with a shorter reaction time.

Further, the present process can obtain dimethylcyclohex-2-ene-1,4-dicarboxylate in a high yield at a lower cost, which is advantageous for mass synthesis of dimethyl terephthalate.

BEST MODE FOR CARRYING OUT THE INVENTION

Process for Cycloaddition of Dimethyl Muconate

The present invention provides a process for cycloaddition of dimethyl muconate, which comprises (1) preparing a reactor filled with ethylene gas; and (2) adding a compound of the following Formula 1 in a solid phase to the reactor and carrying out a cycloaddition reaction to obtain a compound of the following Formula 2.

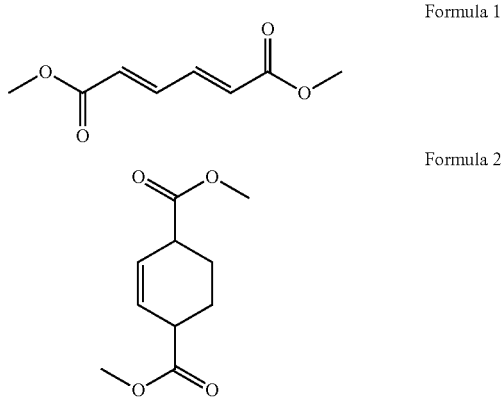

Hereinafter, each step will be described in more detail.

In the above step (1), a reactor filled with ethylene gas is prepared.

The reactor may be a high-temperature and high-pressure reactor.

The reactor may have an internal pressure of 100 bar or more, 120 bar or more, 140 bar or more, 150 bar or more, or 160 bar or more. For example, the reactor may have an internal pressure in the range of 100 to 300 bar, 140 to 250 bar, or 150 to 200 bar. Within the above preferred pressure range, side reactions may be suppressed in the reaction between the compound of Formula 1 and ethylene gas, thereby enhancing the yield.

The reactor may have an internal temperature of 100° C. or higher, 130° C. or higher, 170° C. or higher, 200° C. or higher, or 250° C. or higher. For example, the reactor may have an internal temperature in the range of 100 to 400° C., 130 to 300° C., or 170 to 250° C. Within the above preferred temperature range, it is advantageous from the viewpoint of reaction time that the reactivity may be further enhanced.

The reactor may be filled with ethylene gas only as the gas therein. For example, ethylene gas may be filled in the reactor up to the above pressure range. Further, the reaction may be carried out by continuously maintaining the pressure of ethylene gas during the reaction. In addition, the reactor may be further filled with inert gas.

As a preferred example, the reactor is filled with ethylene gas to a pressure of 5 to 20 bar, the temperature of the reactor is then raised to 170 to 250° C., and ethylene gas is further filled in the reactor to make the internal pressure of the reactor 140 bar or more.

The reactor may be filled with a solvent for the cycloaddition reaction of the compound of Formula 1.

The solvent may be selected from the group consisting of aromatic solvents such as benzene, toluene, chlorobenzene, cresol, methyl phenyl ester, and xylene; alkyl ether solvents such as tetrahydrofuran, dimethyl ethylene glycol, ethylene glycol dimethyl ether, and diglyme; alkyl acetate solvents such as methyl acetate, ethyl acetate, and butyl acetate; ketone solvents such as acetone, methyl ethyl ketone, and cyclohexanone; N-methyl pyrrolidone; methyl formamide; dimethyl sulfoxide; acetonitrile; hydrocarbons such as dodecane and hexadecane; and mixtures thereof. But it is not limited thereto.

Specifically, the solvent may be selected from the group consisting of meta-xylene, tetrahydrofuran, ethyl acetate, dimethyl ethylene glycol, N-methyl pyrrolidone, dimethylsulfoxide, and mixtures thereof.

The solvent may be filled in the reactor in an amount ranging from 1 to 200 equivalents, 5 to 100 equivalents, or 5 to 70 equivalents, based on 1 equivalent of trans,trans-dimethyl muconate to be introduced in a subsequent step.

In the above step (2), a compound of the above Formula 1 (i.e., trans,trans-dimethyl muconate) in a solid phase is introduced to the reactor prepared above, and a cycloaddition reaction is carried out to obtain a compound of the above Formula 2 (i.e., dimethylcyclohex-2-ene-1,4-dicarboxylate).

As used herein, the term "cycloaddition reaction" refers to a reaction in which two or more unsaturated compounds are combined to form a compound having an increased ring while multiple bonds are reduced.

In the conventional process in which ethylene gas is injected after a high concentration of dimethyl muconate is dissolved in a solvent, the yield is low due to many side reactions. According to the present invention, however, since dimethyl muconate in a solid phase is introduced to a reactor filled with ethylene gas in advance, an efficient cycloaddition reaction may take place even under high-concentration conditions without side reactions. Thus, it is possible to obtain the desired target compound in a high yield.

If the reactor is a high-temperature and high-pressure reactor in the preceding step (1), the compound of Formula 1 is preferably introduced into the reactor using a solid injector.

The compound of Formula 1 may be introduced into the reactor at a time or in divided amounts.

Preferably, the compound of Formula 1 may be divided into two or more and then introduced into the reactor. For example, the number of divided introductions may be 2 to 30, 3 to 20, 4 to 15, or 5 to 12. In addition, when the compound of Formula 1 is divided for introduction, the same amount may be introduced each time.

Preferably, the cycloaddition reaction may be carried out at the time of each divided introduction.

That is, the compound of Formula 1 may be introduced into the reactor by a divided amount once, and the cycloaddition reaction may be carried out for a certain period of time. Thereafter, the divided amount of the next time may be introduced into the reactor, and the cycloaddition reaction may be carried out for a certain period of time.

For example, the cycloaddition reaction may be carried out for 30 minutes to 10 hours, 1 to 6 hours, or 1 to 4 hours, at the time of each divided introduction.

If a solvent is filled in the reactor in the preceding step (1), the cycloaddition reaction may be carried out in the solvent. In such event, the total amount of the compound of Formula 1 introduced into the reactor may be 0.5 to 5.0 moles, 1.0 to 3.0 moles, or 1.2 to 2.5 moles, based on 1 liter of the solvent.

If the compound of Formula 1 is divided into two or more and then introduced into the reactor, the amount of the compound of Formula 1 introduced into the reactor at each time may be 0.01 to 1.0 mole, or 0.1 to 0.5 mole, based on 1 liter of the solvent. In addition, the total amount of the compound of Formula 1 divided and introduced into the reactor may be 0.5 to 5.0 moles, 1.0 to 3.0 moles, or 1.2 to 2.5 moles, based on 1 liter of the solvent.

According to a preferred embodiment, the reactor in step (1) may be filled with a solvent for the cycloaddition reaction of the compound of Formula 1 and may have an internal pressure of 140 bar or more and an internal temperature of 170 to 250° C.; in step (2), the compound of Formula 1 may be divided into two or more and then introduced into the reactor, wherein the amount of the compound of Formula 1 introduced into the reactor at each time may be 0.1 to 0.5 mole based on 1 liter of the solvent, the total amount of the compound of Formula 1 divided and introduced into the reactor may be 1.0 to 3.0 moles based on 1 liter of the solvent, and the cycloaddition reaction may be carried out for 1 to 6 hours at the time of each divided introduction.

According to the process of the present invention, it is possible to efficiently carry out the cycloaddition reaction of dimethyl muconate under a higher concentration condition than that of the prior art. As a result, the desired cycloadded compound can be prepared in a high yield and high purity.

For example, the yield of the cycloaddition reaction may be 80% or more, 85% or more, 90% or more, or even 95% or more.

In addition, according to the present process, it is advantageous from the economic viewpoint that it can achieve the same level of reaction efficiency as in the prior art even with shorter reaction times.

Further, the present process can obtain dimethylcyclohex-2-ene-1,4-dicarboxylate in a high yield at a lower cost, which is advantageous for mass synthesis of dimethyl terephthalate.

Process for Preparing Dimethyl Terephthalate

In addition, the present invention provides a process for preparing dimethyl terephthalate, which comprises (1) preparing a reactor filled with ethylene gas; (2) introducing a compound of the following Formula 1 in a solid phase to the reactor and carrying out a cycloaddition reaction to obtain a compound of the following Formula 2; and (3) obtaining dimethyl terephthalate from the compound of Formula 2 through an aromatization reaction.

In the process for preparing dimethyl terephthalate, steps (1) and (2) may be carried out under the same steps and conditions as described in the process for cycloaddition of dimethyl muconate.

In step (3), the compound of Formula 2 (i.e., dimethyl-cyclohex-2-ene-1,4-dicarboxylate) is subjected to an aromatization reaction to obtain dimethyl terephthalate.

For example, the aromatization reaction of the compound of Formula 2 may be carried out in the presence of a metal catalyst using an unsaturated hydrocarbon as an oxidizing agent.

As an unsaturated hydrocarbon is used as an oxidizing agent (or a reduction inhibitor) during the aromatization reaction as described above, hydrogen can be effectively removed in the course of the reaction, thereby suppressing the side reactions as much as possible and increasing the yield of dimethyl terephthalate as a target product.

The unsaturated hydrocarbon may be at least one selected from the group consisting of acetylene, ethylene, propylene, isobutene, and butadiene. As a specific example, the aromatization reaction may be carried out using ethylene gas as an oxidizing agent in the presence of a metal catalyst.

The metal catalyst may be a palladium-based or platinum-based catalyst. In addition, the aromatization reaction may be carried out at a temperature of 50 to 300° C.

Alternatively, the aromatization reaction may be carried out once the compound of Formula 2 has been converted to dimethylcyclohex-1-ene-1,4-dicarboxylate. The conversion may be carried out at a temperature of 50 to 150° C. in the presence of a basic catalyst. If the aromatization reaction is carried out after the conversion as described above, the side reactions can be further suppressed.

Preparation of the Compound of Formula 1

The compound of Formula 1 (i.e., trans,trans-dimethyl muconate) used as a starting material in the process of the present invention may be synthesized from muconic acid or obtained using isomers thereof.

As an example, the compound of Formula 1 may be synthesized from trans,trans-muconic acid in the presence of a catalyst.

In such event, the catalyst that can be used may be selected from the group consisting of acids such as methane sulfonic acid, p-toluenesulfonic acid, phosphoric acid, hydrochloric acid, and sulfuric acid; bases such as potassium carbonate and sodium hydroxide; and mixtures thereof.

In addition, the synthesis of the compound of Formula 1 may be carried out in a solvent. Here, the solvents exemplified in the cycloaddition reaction above may be used.

According to a preferred embodiment, concentrated sulfuric acid as a catalyst is added to trans,trans-muconic acid, followed by reaction under reflux conditions, to prepare the compound of Formula.

As another example, the compound of Formula 1 may be obtained by an isomerization reaction of cis,trans-dimethyl muconate.

Preferably, the compound of Formula 1 may be obtained by an isomerization reaction in the presence of at least one catalyst among the cobalt complex and palladium complex compounds.

The cobalt complex compound may be cobalt sulfide (CoS), cobalt disulfide ($CoS_2$), or mixtures thereof.

In addition, the palladium complex compound may be a compound containing palladium and tritertbutylphosphine, isobutyl chloride, or a mixture thereof as a ligand that is bound to palladium.

In addition, the synthesis of the compound of Formula 1 may be carried out in a solvent. Here, the solvents exemplified in the cycloaddition reaction above may be used.

MODE FOR THE INVENTION

Hereinafter, the present invention is described in more detail by the specific examples and comparative examples. However, these examples are provided only for more specific illustration purposes, and the present invention is not limited thereto.

Preparation Example 1: Synthesis of Cis,Trans-Dimethyl Muconate

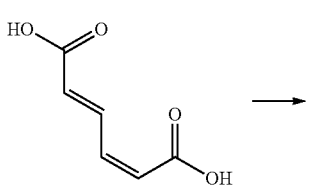

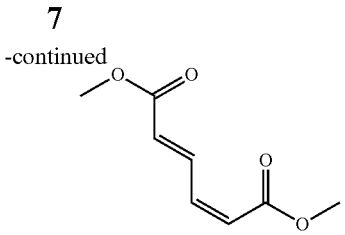

1,000 g of cis,trans-muconic acid was dissolved in 5,000 ml of methanol. 30 g of concentrated sulfuric acid as a catalyst was added to the solution thus obtained, followed by reaction for 16 hours under reflux conditions at 65° C. As a result, 1,160 g of cis,trans-dimethyl muconate was obtained.

Preparation Example 2: Isomerization of Cis,Trans-Dimethyl Muconate to Trans,Trans-Dimethyl Muconate

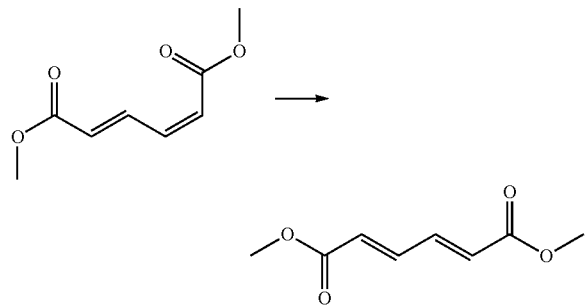

A 5,000-ml round-bottom flask was charged with 766 g of cis,trans-dimethyl muconate obtained in Preparation Example 1, 55.4 g of cobalt disulfide as a catalyst, and 3,000 ml of acetonitrile as a solvent to prepare a cis,trans-dimethyl muconate solution at a concentration of 1.5 M. The solution was subjected to an isomerization reaction for 18 hours under reflux conditions of 82° C. to obtain trans,trans-dimethyl muconate.

Example 1: Cycloaddition of Trans,Trans-Dimethyl Muconate

A 900-ml high-temperature and high-pressure reactor (Parr Reactor, 4533HP) was charged with 500 ml of ethylene glycol dimethyl ether as a solvent and filled with ethylene to reach 20 bar. The temperature inside the reactor was raised to 200° C., and the reactor pressure was maintained at 165 bar by injecting ethylene gas using a gas booster. 42.5 g of trans,trans-dimethyl muconate obtained in Preparation Example 2 was introduced first time to the reactor at high temperature and high pressure using a solid injector, followed by a cycloaddition reaction for 4 hours. Thereafter, 42.5 g of trans,trans-dimethyl muconate was introduced second time using a solid injector, followed by a cycloaddition reaction for 4 hours. Lastly, 42.5 g of trans,trans-dimethyl muconate was introduced third time using a solid injector, followed by a cycloaddition reaction for 4 hours.

Example 2: Cycloaddition of Trans,Trans-Dimethyl Muconate

The cycloaddition reaction was carried out in the same manner as in Example 1, except that the cycloaddition reaction was carried out for 4 hours while 21.25 g of trans,trans-dimethyl muconate was added 6 times.

Example 3: Cycloaddition of Trans,Trans-Dimethyl Muconate

The cycloaddition reaction was carried out in the same manner as in Example 1, except that the cycloaddition reaction was carried out for 4 hours while 12.75 g of trans,trans-dimethyl muconate was added 10 times.

Example 4: Cycloaddition of Trans,Trans-Dimethyl Muconate

The cycloaddition reaction was carried out in the same manner as in Example 1, except that the cycloaddition reaction was carried out for 4 hours while 12.75 g of trans,trans-dimethyl muconate was added 12 times.

Comparative Example 1: Cycloaddition of Trans,Trans-Dimethyl Muconate

A 900-ml high-temperature and high-pressure reactor (Parr Reactor, 4533HP) was charged with a solution in which 127.5 g of trans,trans-dimethyl muconate had been dissolved in 500 ml of ethylene glycol dimethyl ether, followed by a cycloaddition reaction for 4 hours while ethylene gas was being injected.

Test Example 1. Evaluation of the Conversion and Yield of the Cycloaddition Reaction Gas chromatography mass spectrometry (GC-MS) was carried out on the reactants obtained in Examples 1 to 4 and Comparative Example 1 under the following conditions. The conversion (%) of trans,trans-dimethyl muconate was calculated according to the following equation.
Instrument: Claus 680 GC and SQ 8 MS of Perkin Elmer
Column: DB-5 (15 m×0.25 mm×0.10 μm, Agilent Technologies, USA)

Conversion (%)=100−[(GC-MS area of trans,trans-dimethyl muconate/GC-MS area of total reactants)×100]

In addition, to confirm the actual yield, fractional distillation was carried out to measure the yield (%) of dimethylcyclohex-2-ene-1,4-dicarboxylate under the following conditions.
Degree of vacuum: 150 mTorr
Distillation temperature: 130° C.
The results are summarized in Table 1 below.

TABLE 1

| | Concentration of total reactants | No. of divided introductions | Conversion (%) | Yield (%) |
|---|---|---|---|---|
| Ex. 1 | 1.5M | 3 times | 87 | 85 |
| Ex. 2 | 1.5M | 6 times | 96 | 94 |
| Ex. 3 | 1.5M | 10 times | 98 | 97 |
| Ex. 4 | 1.8M | 12 times | 98 | 97 |
| C. Ex. 1 | 1.5M | Once | 78 | 77 |

As shown in Table 1, when the compound of Formula 1 in a solid phase was introduced to the reactor filled with ethylene gas as in Examples 1 to 4, the conversion and yield were very excellent even at a high concentration of 1.5 M or more.

In particular, when the compound of Formula 1 was reacted while being divided into several times under the same high concentration conditions, it was confirmed that the cycloaddition reaction took place more efficiently with a lower extent of side reactions.

In contrast, when the cycloaddition reaction was carried out in the conventional manner as in Comparative Example 1, it was confirmed that the conversion and yield were low under the high concentration conditions and that the reaction was not efficient with a higher extent of side reactions.

The invention claimed is:

1. A process for cycloaddition of dimethyl muconate, which comprises:
    (1) preparing a reactor filled with ethylene gas; and
    (2) introducing a compound of the following Formula 1 in a solid phase to the reactor and carrying out a cycloaddition reaction to obtain a compound of the following Formula 2

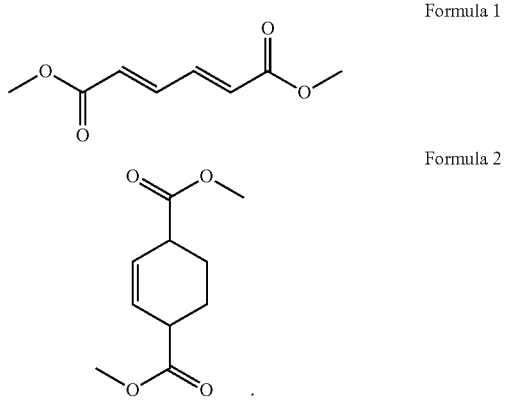

2. The process for cycloaddition of dimethyl muconate of claim 1, wherein the reactor in step (1) has an internal pressure of 140 bar or more.

3. The process for cycloaddition of dimethyl muconate of claim 1, wherein the reactor in step (1) has an internal temperature of 170 to 250° C.

4. The process for cycloaddition of dimethyl muconate of claim 1, wherein in step (2), the compound of Formula 1 is divided into two or more and then introduced into the reactor.

5. The process for cycloaddition of dimethyl muconate of claim 4, wherein the cycloaddition reaction is carried out for 1 to 6 hours at the time of each divided introduction.

6. The process for cycloaddition of dimethyl muconate of claim 1, wherein the reactor in step (1) is filled with a solvent for the cycloaddition reaction of the compound of Formula 1.

7. The process for cycloaddition of dimethyl muconate of claim 6, wherein the total amount of the compound of Formula 1 divided and introduced into the reactor is 1.0 to 3.0 moles based on 1 liter of the solvent, and the yield of the cycloaddition reaction is 85% or more.

8. The process for cycloaddition of dimethyl muconate of claim 6, wherein in step (2), the compound of Formula 1 is divided into two or more and then introduced into the reactor; and
    the amount of the compound of Formula 1 introduced into the reactor at each time is 0.1 to 0.5 mole based on 1 liter of the solvent.

9. The process for cycloaddition of dimethyl muconate of claim 8, wherein the total amount of the compound of Formula 1 divided and introduced into the reactor is 1.0 to 3.0 moles based on 1 liter of the solvent.

10. The process for cycloaddition of dimethyl muconate of claim 6, wherein the solvent is selected from the group consisting of meta-xylene, tetrahydrofuran, ethyl acetate, dimethyl ethylene glycol, N-methyl pyrrolidone, dimethylsulfoxide, and mixtures thereof.

11. The process for cycloaddition of dimethyl muconate of claim 1, wherein the reactor in step (1) is filled with a solvent for the cycloaddition reaction of the compound of Formula 1 and has an internal pressure of 140 bar or more and an internal temperature of 170 to 250° C.; and
    in step (2), the compound of Formula 1 is divided into two or more and then introduced into the reactor, wherein the amount of the compound of Formula 1 introduced into the reactor at each time is 0.1 to 0.5 mole based on 1 liter of the solvent, the total amount of the compound of Formula 1 divided and introduced into the reactor is 1.0 to 3.0 moles based on 1 liter of the solvent, and the cycloaddition reaction is carried out for 1 to 6 hours at the time of each divided introduction.

12. A process for preparing dimethyl terephthalate, which comprises:
    (1) preparing a reactor filled with ethylene gas;
    (2) introducing a compound of the following Formula 1 in a solid phase to the reactor and carrying out a cycloaddition reaction to obtain a compound of the following Formula 2; and
    (3) obtaining dimethyl terephthalate from the compound of Formula 2 through an aromatization reaction

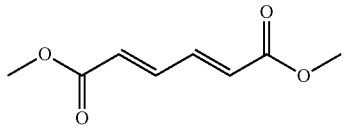

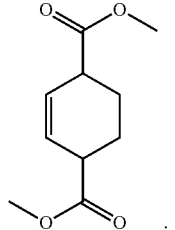

* * * * *